United States Patent
Pricone

(10) Patent No.: US 9,962,535 B2
(45) Date of Patent: May 8, 2018

(54) HOLLOW SILICA GLASS MICRONEEDLE ARRAYS AND METHOD AND APPARATUS FOR MANUFACTURING SAME

(71) Applicant: 10x Technology LLC, Libertyville, IL (US)

(72) Inventor: Robert M. Pricone, Libertyville, IL (US)

(73) Assignee: 10x TECHNOLOGY LLC, Libertyville, IL (US)

( * ) Notice: Subject to any disclaimer, the term of this patent is extended or adjusted under 35 U.S.C. 154(b) by 625 days.

(21) Appl. No.: 14/400,504

(22) PCT Filed: May 10, 2013

(86) PCT No.: PCT/US2013/040579
§ 371 (c)(1),
(2) Date: Nov. 11, 2014

(87) PCT Pub. No.: WO2013/170171
PCT Pub. Date: Nov. 14, 2013

(65) Prior Publication Data
US 2015/0141924 A1    May 21, 2015

Related U.S. Application Data

(60) Provisional application No. 61/646,050, filed on May 11, 2012.

(51) Int. Cl.
*A61M 37/00* (2006.01)
*C03B 19/09* (2006.01)
*C03B 9/29* (2006.01)

(52) U.S. Cl.
CPC ......... *A61M 37/0015* (2013.01); *C03B 19/09* (2013.01); *A61M 2037/003* (2013.01);
(Continued)

(58) Field of Classification Search
None
See application file for complete search history.

(56) References Cited

U.S. PATENT DOCUMENTS 5,948,535 A    9/1999   Chiurlo et al.
7,211,062 B2   5/2007   Kwon
(Continued)

OTHER PUBLICATIONS

International Report on Patentability dated Nov. 11, 2014 for PCT/US2013/040579 filed May 10, 2013.

*Primary Examiner* — Mary Lynn F Theisen
(74) *Attorney, Agent, or Firm* — McDonnell Boehnen Hulbert & Berghoff LLP

(57) ABSTRACT

A novel array of hollow silica glass microneedles is provided. The array is prepared from a silica dispersion. A novel apparatus is provided comprising a negative mold component having tapered openings therein and a positive mold component having positive elements that are received within the tapered openings of the negative mold component. An assembly is prepared of the negative mold component and the positive mold component, with an aqueous silica dispersion received within the space between the outer surface of the positive elements and the inner surface of the openings. The assembly is heated to remove air and water vapors from the silica dispersion, then the assembly is further heated to sinter the remaining silica to silica glass. The sintered silica glass when removed from the mold components is in the form of an array of microneedles.

11 Claims, 3 Drawing Sheets

(52) U.S. Cl.
CPC .............. *A61M 2037/0023* (2013.01); *A61M 2037/0053* (2013.01)

(56) References Cited

U.S. PATENT DOCUMENTS

| | | |
|---|---|---|
| 8,029,887 B2 | 10/2011 | Costa et al. |
| 2002/0138049 A1 | 9/2002 | Allen et al. |
| 2003/0009113 A1 | 1/2003 | Olson |
| 2004/0007796 A1 | 1/2004 | Lastovich |
| 2004/0019331 A1 | 1/2004 | Yeshurun |
| 2006/0202385 A1 | 9/2006 | Xu et al. |
| 2007/0023386 A1 | 2/2007 | Kravitz et al. |
| 2007/0161964 A1 | 7/2007 | Yuzhakov |
| 2009/0131905 A1* | 5/2009 | Allen ................ A61B 5/14514 604/501 |
| 2010/0193997 A1 | 8/2010 | Frederickson et al. |

\* cited by examiner

HOLLOW SILICA GLASS MICRONEEDLE ARRAYS AND METHOD AND APPARATUS FOR MANUFACTURING SAME

This application is a U.S. national phase application of International Patent Application No. PCT/US2013/040579, filed on May 10, 2013, which claims the benefit of Provisional Patent Application Ser. No. 61/646,050, filed May 11, 2012, entitled "Method and Apparatus for Manufacturing Hollow Silica Glass Microneedle Arrays."

BACKGROUND OF THE INVENTION

Transdermal drug delivery is a diverse emerging field that will require a broad range of microneedle structures and materials. Hollow microneedles are a particularly significant aspect of this technology that present fabrication challenges for designers of microneedle arrays.

Patches containing arrays of microneedles are being investigated by many entities. It is known that the skin to be penetrated by microneedles for the delivery of a drug includes many layers that may vary in thickness. The outermost layer of the skin is the stratum corneum, which is usually between 10 and 20 microns (10-20 µm) thick. This layer presents the greatest barrier to transdermal flux of drugs or other molecules into the body. Below the stratum corneum is the epidermal layer which may be between 50 and 100 µm thick. Immediately below the epidermis is the dermis which is between 1 and 3 mm thick. A more detailed description of the skin layers and the desired range of dimensions of microneedle arrays is found in U.S. Pat. No. 7,211,062 B2 at columns 3 and 4, the disclosure of which is incorporated herein by reference in its entirety.

Transdermal patches of the prior art typically are manufactured from polymers that exhibit high rheology, even at elevated temperatures. The challenge in manufacturing a patch containing arrays of microneedles lies in accurately forming these high rheology polymers into very small, precise microneedle structures of high-aspect ratio. It is particularly difficult to use such high rheology polymers to form microneedle arrays having fine channels running through their length that allow a drug to pass through the microneedle to be delivered to the skin of a user. There are also concerns regarding potential polymer interactions and biocompatibility through clinical testing requirements.

SUMMARY OF THE INVENTION

This present invention provides novel arrays of hollow silica glass microneedles, and a novel method and apparatus for manufacturing such needles and arrays with precision. In accordance with the present invention, the arrays are molded in a novel molding apparatus from ultra-low viscosity aqueous silica dispersions sometimes referred to in the art as "sol gels." These aqueous silica dispersions which have near water-like viscosity, quickly take on the shape of the mold at ambient temperatures and can then be cured to a hard, strong, chemically resistant silica glass device capable of delivering a drug transdermally. The use of these aqueous silica dispersions allows for the manufacture of hollow microneedles with high aspect ratios.

The use of silica glass affords advantages over polymer substrates and other materials typically used for microneedles. The novel hollow silica glass microneedle arrays can be cleaned after use, sterilized and re-used multiple times. Potential interaction of a polymer microneedle with drugs is eliminated. The microneedle shape is accurate and the needle tips can be very sharp, minimizing the pressure required to penetrate the first skin layer as well as minimizing discomfort.

Another advantage is that larger diameter channels can be achieved for increased drug delivery since the silica glass walls are strong enough to maintain the strength of the microneedles compared to polymer substrates.

Although the use of silica glass has been proposed to produce a patch containing an array of solid microneedles, a means to provide a hollow silica microneedle drug delivery system has not been proposed.

DETAILED DESCRIPTION OF THE INVENTION

Figure 1:
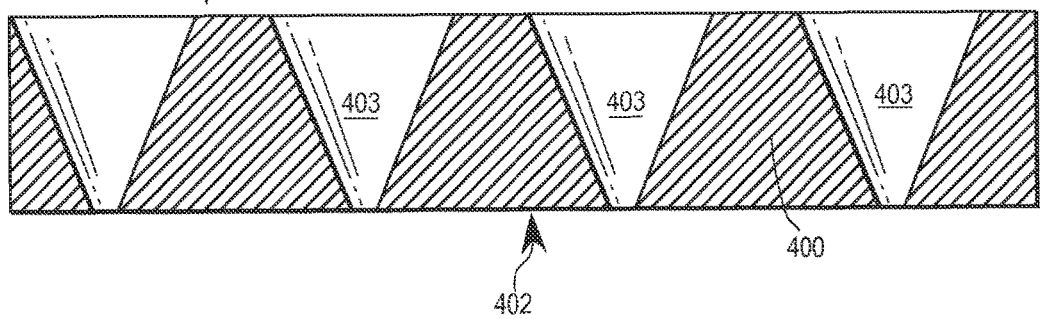
FIG. 1 is representative of a partial elevational cross section of a negative mold element used in the present invention.

In one embodiment, the invention relates to an array of silica glass microneedles having a channel therein for drug delivery. In a preferred embodiment the channel is in the form of a hollow passage disposed longitudinally within the body of the microneedle. In another preferred embodiment the array of microneedles is provided as a patch containing an array of microneedles.

In one embodiment the microneedles in the array have a center-to-center spacing of about 200-500 microns, preferably about 250-400 microns, and most preferably about 360 microns. In one embodiment the microneedles have a height of about 100-900 microns, preferably about 100-700 microns, more preferably about 150-400 microns, and most preferably about 200 microns. In one embodiment the microneedles have a base diameter of about 100-500 microns, more preferably of about 100-250 microns, and most preferably of about 160 microns. In one embodiment the microneedles have a taper angle of about 10-20 degrees, preferably about 12-18 degrees, and more preferably about 15 degrees. In one embodiment the hollow channel within the microneedle has an opening of about 10-30 microns at the base of the microneedle and about 1-3 microns at the tip of the microneedle.

In one embodiment, the invention relates to a method of forming hollow silica glass microneedles, the method comprising the steps of providing a negative mold component having upper and lower surfaces and having at least one tapered opening formed therein with the narrow end of the taper exiting at the lower surface of the mold; introducing an aqueous silica dispersion into said tapered opening; providing a complementary positive mold component having at least one tapered element extending therefrom and formed to be placed within the tapered opening of the negative mold component and being uniformly spaced from the tapered opening to provide an assembly with a gap between the outer surface of the tapered element and the inner surface of the tapered opening in which the tapered element is positioned, with the end of the tapered element extending beyond said bottom surface of the negative mold component; removing water from the aqueous silica dispersion to leave a silica deposit; sintering the silica deposit at a temperature and for a time sufficient to cure the silica to a glass state; removing the positive mold element from the assembly; and removing the hollow silica glass microneedle array from the negative mold component.

In one embodiment of the invention, a novel apparatus for making an array of hollow silica microneedles comprises two complementary mold components that fit together to define an array of microneedles having channels through the microneedles. The mold component having openings that hold the silica dispersion to form the outer surface of the microneedles is referred to herein as the negative mold component and the mold component having positive elements that form channels through the microneedles is referred to herein as the positive mold component. When assembled to form the hollow silica microneedles the positive elements of the positive mold component fit within the openings of the negative mold component. The mold components typically are fabricated from nickel or nickel alloys to provide strength and to maintain the form of the positive and negative mold components at elevated temperatures.

Further in accordance with the invention, hollow silica microneedle arrays are fabricated from aqueous silica dispersions sometimes known in the art as "sol gels," which are known to be useful, for example, in the art of manufacturing optical elements, as disclosed in U.S. Pat. No. 5,948,535 and U.S. Pat. No. 8,029,887, the disclosures of which are incorporated herein by reference in their entireties. Such dispersions may comprise water, silicon oxide and optionally at least one oxide of a different element.

FIG. 1 is a partial elevation cross-sectional view of a negative mold component 400 with multiple tapered openings 403 extending between the upper surface 401 and bottom surface 402 of the mold. The tapered openings can be either conical or pyramidal in three-dimensional shape. The tapered openings 403 are formed with the aspect ratio, needle height and width each selected to compensate for shrinkage of the aqueous dispersion during the microneedle manufacturing process as described herein.

Figure 2:
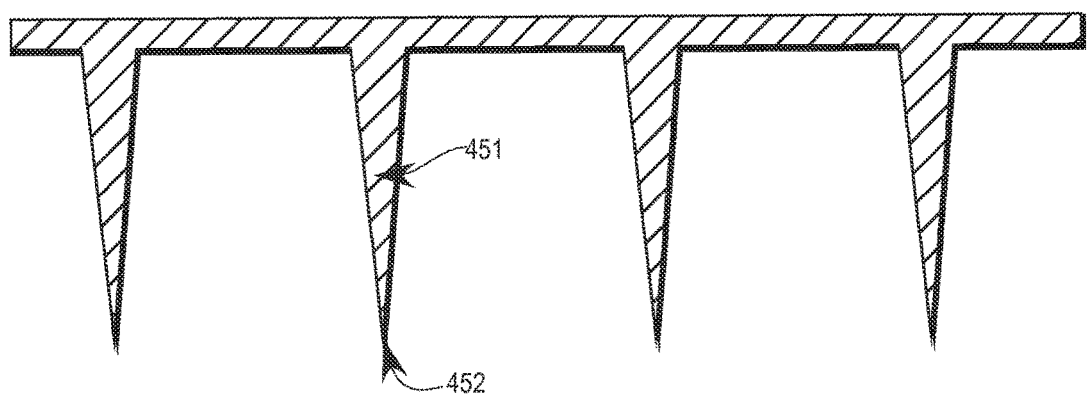
FIG. 2 is representative of a partial elevational cross section of a positive mold element used in the present invention.
Figure 6:
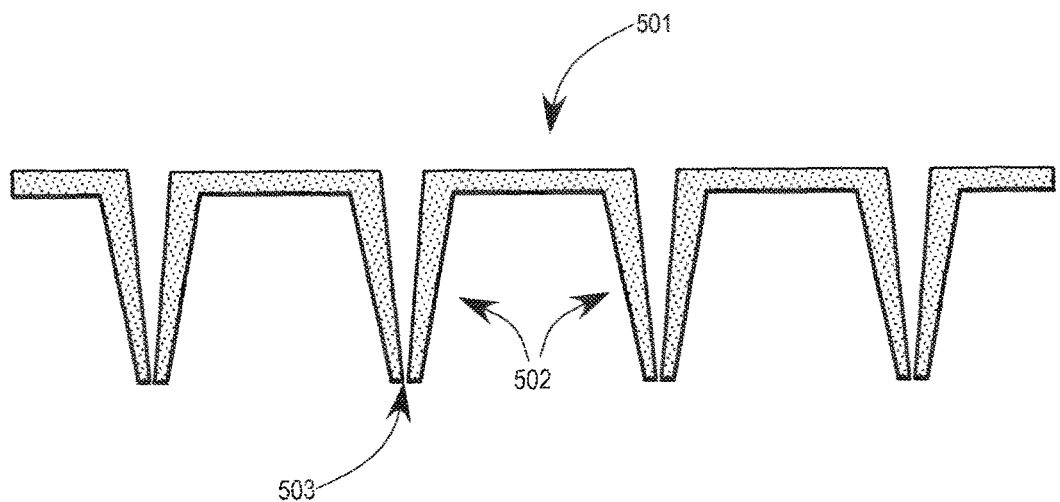
FIG. 6 is a cross sectional view of the microneedle array depicted in FIG. 4B, taken in the direction of the arrow 6-6 in FIG. 4B.

FIG. 2 is a partial elevation cross-sectional view of a positive mold 450 component comprising tapered positive elements 451 having tips 452, the elements 451 being sized and dimensioned to be inserted into tapered openings 403 of negative mold component 400, to form the channel structures 503 in the finished microneedles 502 in FIG. 6.

Figure 3:
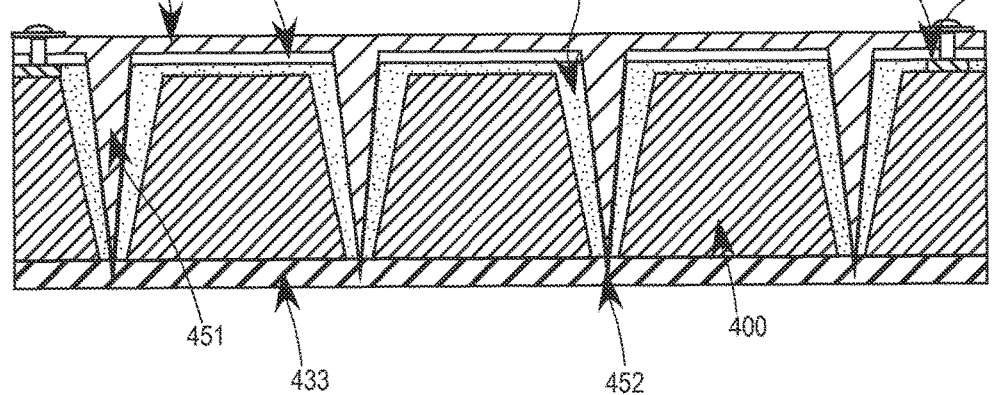
FIG. 3 is representative of a partial elevational cross sectional view of the assembled mold elements and other components used in the present invention.

FIG. 3 illustrates the assembled mold components 400 and 450. An inert flexible gasket 433 which can be made, for example, from silicone rubber covers the bottom surface 402 of negative mold component 400. In accordance with the inventive method, an aqueous silica dispersion 434 is introduced into the tapered openings 403, complementary positive mold component 450 is accurately located over the negative mold component 400 so that the positive elements 451 can be disposed within the tapered openings 403 with a gap between the outer surface of positive elements 451 and the inner surface of openings 403, the gap being filled with the silica dispersion 434. Accurate location of the two mold components 400 and 450 is achieved using locating guide pins 436 between the negative and positive molds components. Gaskets 437 around the locating guide pins 436 determine the space between mold components 400 and 450 that will be occupied with the silica dispersion which forms the backing of the hollow microneedle array. Once the mold components are assembled as shown in FIG. 3 the assembly is heated for a time and at a temperature sufficient to remove water from the dispersion thereby leaving a silica deposit. Then the assembly is heated for a time and at a temperature sufficient to sinter the deposit silica so that it is cured to form silica glass. The times and temperatures for the step of removing water and the step of sintering will be readily determined by those of skill in the art.

In the embodiment illustrated in FIG. 3, the tips 452 of the positive mold elements 451 extend into the silicone rubber gasket 433 at the small end of the tapered opening 403 in the mold component 400, thus sealing the silica dispersion 434 in the gap between the outer surface of element 451 and the inner surface of the opening 403 when the mold components 400 and 450 are assembled, and the tips 452 extend beyond the silica dispersion to insure the tip of the finished needle 502 is open.

A porous air and vapor membrane 438 is provided between the lower surface of the positive mold component 450 and the upper surface 401 of negative mold component 400. The membrane 438 allows air bubbles and water vapor to escape from the dispersion as the water in the silica dispersion is evaporated away in the subsequent heating and sintering steps.

Because a large volume of the silica dispersion 434 is water, shrinkage will occur during the heating step as the water is removed, causing the final dimension of the microneedles to be 50% or less than the original volume defined by the gap formed between the positive elements 451 and the openings 403. The gap is not numbered in the drawings submitted herewith but is visualized by the area occupied by the dispersion 434 in FIG. 3. The shrinkage is predictable and can be compensated for by designing the dimensions of the mold components 400 and 450 so that the gap between positive elements 451 and openings 403 holds a sufficient volume of the silica dispersion to shrink down to the desired final dimensions. The apparatus as described herein can be used to form hollow silica microneedles in accordance with the "sol-gel" process used to form optical articles as described in the aforementioned U.S. Pat. No. 8,029,887 B2, the disclosure of which is incorporated by reference in its entirety herein. As disclosed therein, isotropy and dimensional tolerances are controlled to optical tolerance by reverse symmetry. Given this predictable dimensional change the positive and negative mold components will have dimensional tolerances larger than those required for the final microneedles. As an example, if the final microneedles are to be 600 microns tall with a base of 160 microns in diameter and a tip 1 micron in diameter, resulting in a 15 degree angle to the base, the array having a center to center spacing of 360 microns, correspondingly larger mold dimensions would be required.

Figure 4A:
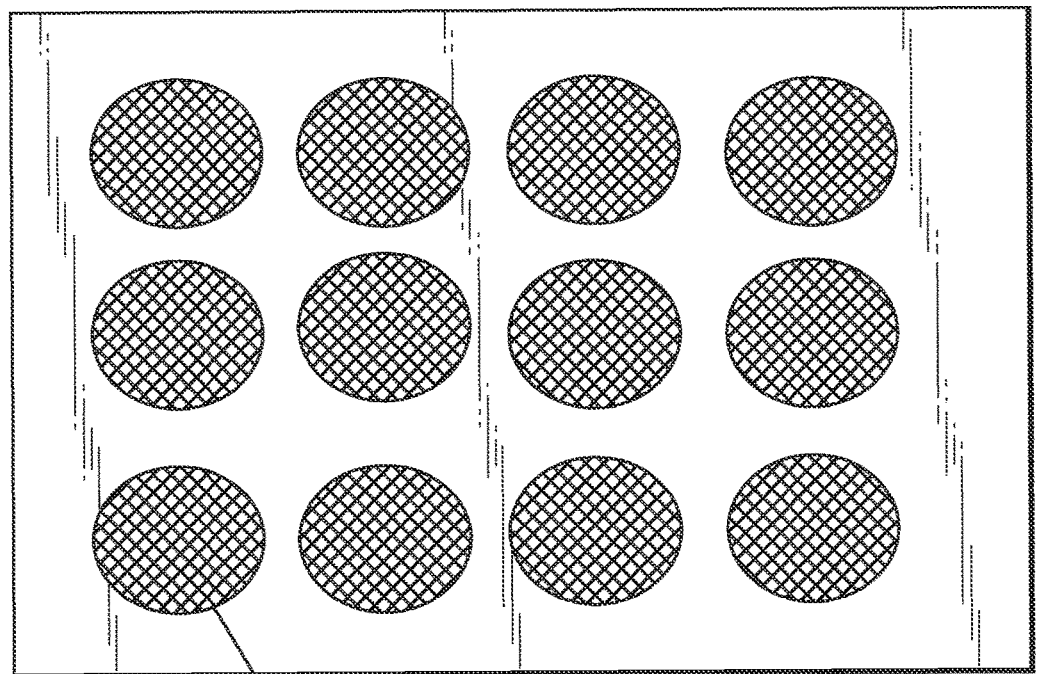
FIG. 4A is a plan view showing a group of formed patches each containing an array of silica glass microneedles formed in accordance with the present invention.
Figure 4B:
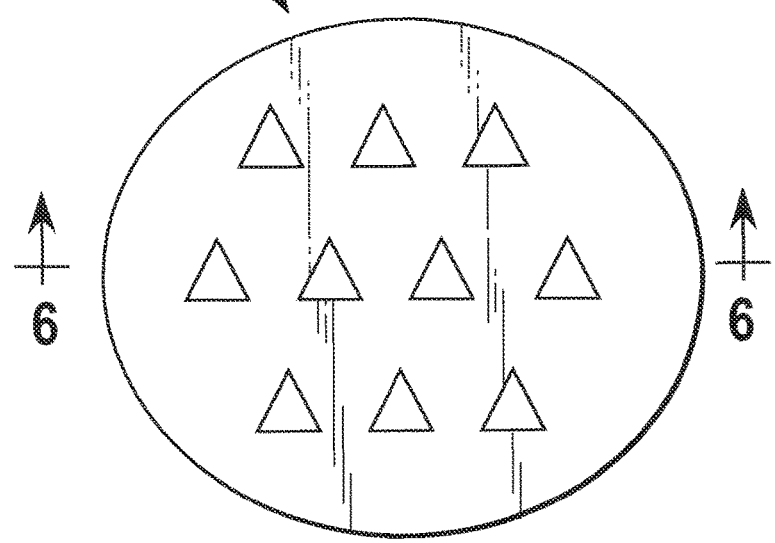
FIG. 4B is an enlarged schematic representation in plain view of one patch containing an array of microneedles from the group illustrated in FIG. 4A.

Once the silica dispersion 434 is in a glass state the positive mold component 450 can be removed leaving hollow channels in the glass microneedles. The array of hollow microneedles is then removed from negative mold component 400, allowing the mold components to be reused. Joining multiple mold assemblies together into larger and larger groups of patches of arrays, as depicted in FIGS. 4A and 4B, allows the process to be scaled to mass production. Batch sizes up to 10,000 groups of patches of arrays per square meter can be achieved by this process.

Figure 5:
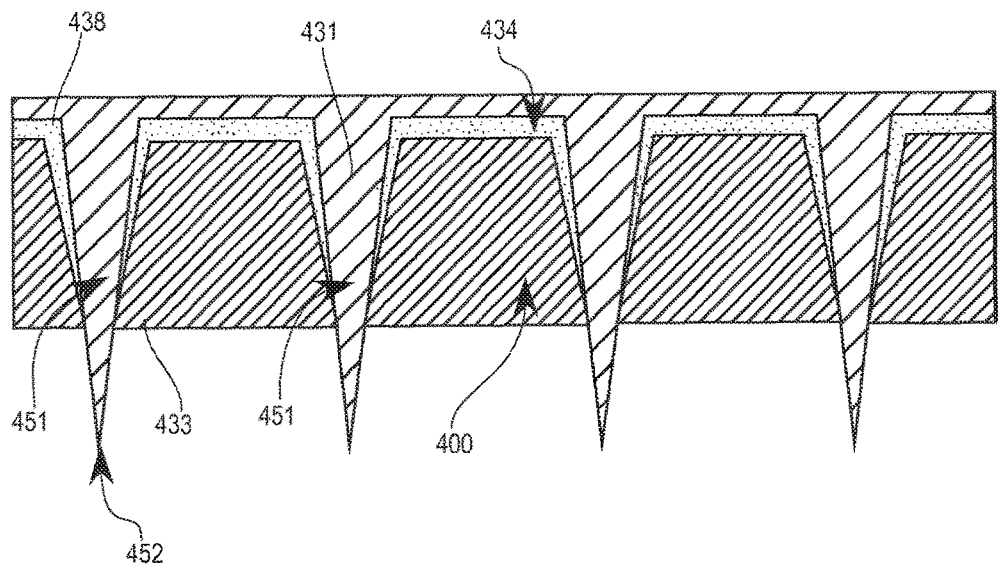
FIG. 5 is representative of a partial cross sectional view of a second embodiment of assembled elements used to produce the silica glass microneedles of the present invention.

FIG. 5 illustrates a second embodiment of an apparatus to provide similar hollow microstructured needles. The negative mold component 400 is similar to the previous version having upper and lower surfaces 401 and 402 and the tapered openings 403 therein. Similarly, positive mold component 450 includes positive elements 451 having tips 452. In this embodiment, the tip 452 of the positive mold element 451 is designed to seal the smaller opening at the bottom of the opening 403 thereby trapping the silica dispersion in the gap formed between the positive element 451 and the walls of the opening 403. Once contained, the water in the silica dispersion is removed through the porous membrane 438 which allow the water to be removed but contains the silica dispersion between the assembled mold components 400 and 450. The remaining deposited silica is then sintered as described in the previous embodiment. To anyone skilled in microstructure molding or microreplication, other variations of this invention will be obvious and suitable now that the novel principle has been described.

FIG. 6 illustrates a portion of a patch depicting the final silica glass microneedle array 501 having the hollow channels 503 and side walls 502 defining the microneedles and having dimensional tolerances consistent with typical designs being tested for this field of use by others.

For exemplary purposes, the openings 403 depicted herein are in the shape of a cone; but other cross sectional shapes (such as pyramidal or square for example) can be utilized. The shape of the positive element 451 ideally is conical to provide a smooth bore or hollow channel 503 in the finished microneedle.

Microneedle height, diameter, aspect ratio and other geometries will change as defined by those who are skilled in transdermal drug delivery. Typical microneedle height ranges from 100 microns to 900 microns depending on the amount of drug to be delivered. A preferred size is 200 microns tall. The size and designs are only limited by the ability to fabricate molds required by this process.

What is claimed is:

1. A method of forming a hollow silica glass microneedle, comprising the steps of:
   providing a negative mold component having upper and lower surfaces and having at least one tapered opening formed therein with the narrow end of the taper exiting at said lower surface of said lower mold component;
   introducing a silica dispersion into said tapered opening;
   providing a complementary positive mold component having at least one tapered element formed to be placed within said tapered opening of said negative mold component and being spaced from said opening to provide an assembly with a gap between the outer surface of the tapered element and the inner surface of the tapered opening with the end of said tapered element extending beyond said bottom surface of the negative mold component;
   removing water from said dispersion to leave a silica deposit;
   sintering the silica deposit to cure the silica to a glass state, thereby forming a hollow glass microneedle;
   removing the positive mold element from said assembly;
   removing the hollow silica glass microneedle from said negative mold component.

2. The method of claim 1, further including the step of placing a silicone rubber gasket below the lower surface of said negative mold component with the tip of said tapered element extending into said gasket before introducing said silica dispersion into said tapered opening, thereby sealing said opening but insuring that the needle formed remains hollow.

3. The method of claim 1, further including the step of placing the end of the tapered element of the positive mold component into the tapered opening of the negative mold component such that the exterior of the tapered element engages the opening in said lower surface of said negative mold component with the end of said element extending beyond said lower surface, thereby sealing the opening in the lower surface so the silica dispersion does not leak out, while insuring that the hollow needle formed remains hollow.

4. The method of claim 1, further including the step of providing a porous membrane between said upper surface of said negative mold component and a surface of said positive mold component to allow air bubbles and water vapor to escape as the water in the silica dispersion is removed.

5. The method of claim 1, wherein the hollow silica glass microneedle has a height in the range of about 100-900 microns.

6. The method of claim 1, wherein the hollow silica glass microneedle has a taper angle of about 10-20 degrees.

7. The method of claim 1, wherein the hollow silica glass microneedle has a channel formed therein, extending from a base of the microneedle to a tip of the microneedle, the channel having an opening of about 10-30 microns at the base of the microneedle and an opening of about 1-3 microns at the tip of the microneedle.

8. The method of claim 1, wherein said microneedle has a height of about 100-900 microns, a base diameter of about 100-500 microns, and a taper angle of about 10-20 degrees to said base.

9. The method of claim 1, wherein
   the negative mold component has a plurality of the tapered openings formed therein;
   the silica dispersion is introduced into said tapered openings; and
   the complementary positive mold component has a plurality of the tapered elements formed to be placed within the tapered openings of said negative mold component;
   wherein the method forms a patch comprising an array of the silica glass microneedles.

10. The method of claim 9, wherein the microneedles have a center-to-center spacing of about 200-500 microns.

11. The method of claim 9, wherein each microneedle has a height of about 100-900 microns, a base diameter of about 100-500 microns, and a taper angle of about 10-20 degrees to said base.

* * * * *